United States Patent [19]
Golan et al.

[11] Patent Number: 5,669,396
[45] Date of Patent: Sep. 23, 1997

[54] METHODS OF DETECTING AND TREATING VASO-OCCLUSIVE CRISIS IN SICKLE CELL DISEASE

[75] Inventors: David Eric Golan, Brookline; Hemant Sadashiv Thatte, Norwood; Alexandru Cristian Bageac, Brookline, all of Mass.

[73] Assignee: President and Fellows of Harvard College, Cambridge, Mass.

[21] Appl. No.: 585,698

[22] Filed: Jan. 16, 1996

[51] Int. Cl.$^6$ ............................................. A61B 19/00
[52] U.S. Cl. ........................... 128/898; 514/814; 514/815
[58] Field of Search .......................... 128/898; 424/529; 436/66, 547, 548, 811; 514/814, 815

[56] References Cited

U.S. PATENT DOCUMENTS

| | | |
|---|---|---|
| 4,157,723 | 6/1979 | Granzow et al. . |
| 4,265,280 | 5/1981 | Ammann et al. . |
| 4,321,919 | 3/1982 | Edelson . |
| 4,412,835 | 11/1983 | Spencer . |

OTHER PUBLICATIONS

B. Brown, *Hematology: Principles and Procedures*, 3rd Edition (1980) (Lea & Febiger, Philadelphia) (pp. 242–243).

R.P. Hebbel and N. Mohandas, "Sickle Cell Adherence," In: *Sickle Cell Disease: Basic Principles and Clinical Practice*, Chapter 16 (1994) (Raven Press, NY) (pp. 217–230).

R. Hoover et al. "Adhesion of Normal and Sickle Erythrocytes to Endothelial Monolayer Cultures," *Blood* 54:872 (1979).

R.P. Hebbel and W.J. Miller "Phagocytosis of Sickle Erythrocytes: Immunologic and Oxidative Determinants of Hemolytic Anemia," *Blood* 64:733 (1984).

C.M. Smith et al. "Pluronic F–68 Reduces the Endothelial Adherence and Improves the Rheology of Liganded Sickle Erythrocytes," *Blood* 69:1631 (1987).

S. Charache et al. "Effect of Hydroxyurea on the Frequency of Painful Crisis in Sickle Cell Anemia," *New Eng. J. Med.* 332:1317 (1995).

F. Sanchez–Madrid et al., "Three Distinct Antigens Associated with Human T–Lymphocyte–Mediated Cytolysis: LFA–1, LFA–2, and LFA–3," *Proc. Nat. Acad. Sci.* 79:7489 (1982).

M.L. Plunkett et al., "Rosetting of Activated Human T–Lymphocytes with Autologous Erythrocytes. Definition of the Receptor and Ligand Molecules as CD2 and Lymphocyte Function–Associated Antigen 3 (LFA–3)," *J. Exp. Med.* 165:664 (1987).

M.R. van Schravendijk et al., "Normal Human Erythrocytes Express CD36, an Adhesion Molecule of Monocytes, Platelets, and Endothelial Cells," *Blood* 80:2105 (1992).

D. Sugihara et al., "Thrombospondin Mediates Adherence of CD36+ Sickle Reticulocytes to Endothelial Cells," *Blood* 80:2634–2642 (1992).

T.M. Wick et al., "Unusually Large von Willebrand Factor Multimers Preferentially Promote Young Sickle and Non-sickle Erythrocyte Adhesion to Endothelial Cells," *Am. J. Hematology* 42:284–292 (1993).

H.A. Brittain et al., "Thrombospondin From Activated Platelets Promotes Sickle Erythrocyte Adherence to Human Microvascular Endothelium Under Physiologic Flow: A Potential Role for Platelet Activation in Sickle Cell Vaso–Occlusion," *Blood* 81:2137–2143 (1993).

(List continued on next page.)

*Primary Examiner*—Vincent Millin
*Assistant Examiner*—Kelly R. O'Hara
*Attorney, Agent, or Firm*—Medlen & Carroll, LLP

[57] ABSTRACT

Methods are described for treating sickle cell disease, and in particular, detection and treatment of vaso-occlusive crisis in sickle cell disease. Antibodies are employed which bind competitively and suppress adhesion of sickle erythrocytes to autologous lymphocytes.

17 Claims, 5 Drawing Sheets

OTHER PUBLICATIONS

C.C. Joneckis et al., "Integrin $\alpha_4\beta_1$ and Glycoprotein IV (CD36) Are Expressed on Circulating Reticulocytes in Sickle Cell Anemia" Blood 82:3548–3555 (1993).

B.E. Gee and O.S. Platt, "Sickle Cell Reticulocytes Adhere to VCAM–1," Blood 85:268–274 (1995).

M.E. Fabry et al., "A Second Generation Transgenic Mouse Model Expressing Both Hemoglobin S (HbS) and HbS–Antilles Results in Increased Phenotypic Severity," Blood 86: 2419–2428 (1995).

T.M. Wick et al., "Molecular basis of sickle cell–endothelial cell interactions," Curr. Op. Hematology 3:118–124 (1996).

FIG. 1 (Data Through 8/16/95)

FIG. 2 (Data Through 10/11/95)

FIG. 3 (Data Through 12/31/95)

FIG. 4 (Data Through 10/17/95)

FIG. 5 (Data Through 12/31/95)

FIG. 6 (Data Through 8/16/95)

FIG. 7 (Data Through 10/17/95)

FIG. 8 (Data Through 12/31/95)

METHODS OF DETECTING AND TREATING VASO-OCCLUSIVE CRISIS IN SICKLE CELL DISEASE

FIELD OF THE INVENTION

The present invention relates to methods for treating sickle cell disease, and in particular, detection and treatment of vaso-occlusive crisis in sickle cell disease.

BACKGROUND

Human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia or sickle cell disease.

In sickle cell anemia, the erythrocytes tend to "sickle" at low oxygen tensions, i.e., to assume a crescent, "holly-leaf" or other abnormal shape instead of the biconcave disc conformation of normal erythrocytes. It is believed that the defective hemoglobin polymerizes and thereby distorts the cell shape, allowing secondary membrane abnormalities including calcium ($Ca^{++}$) influx, i.e., an influx beyond what the calcium pump can handle, potassium ($K^+$) efflux, altered transbilayer phospholipid distribution, membrane protein aggregation, cellular dehydration, and autologous antibody deposition, among others. The result is cell damage, cell rigidity, abnormal cell function and ultimately premature cell death.

The symptoms of sickle cell anemia rarely occur prior to about six months of age. However, the disease is often fatal by the age of 30 years. During the course of the disease, clinical crises occur; these are characterized by severe pain and organ dysfunction most commonly in the long bones and joints, but also in the chest and abdomen and rarely in the brain and heart. Such crises are thought to be due to occlusion of some of the small blood vessels supplying the relevant organ(s). See B. Brown, *Hematology: Principles and Procedures*, 3rd Edition (1980) (Lea & Febiger, Philadelphia) (pp. 242-243).

The mechanism of microvascular occlusion (or "vaso-occlusion") is not precisely known, however, the sickle erythrocyte's predilection for abnormal cell-cell interactions is viewed to be a likely cause. See R. P. Hebbel and N. Mohandas, "*Sickle Cell Adherence,*" In: *Sickle Cell Disease: Basic Principles and Clinical Practice*, Chapter 16 (1994) (Raven Press, N.Y.) (pp. 217–230). For example, it has been known since as early as 1979 that sickle erythrocytes adhere to endothelial cells. See R. Hoover et al. "Adhesion of Normal and Sickle Erythrocytes to Endothelial Monolayer Cultures," *Blood* 54:872 (1979). There are also reports that sickle erythrocytes interact with monocytes/macrophages. See R. P. Hebbel and W. J. Miller "Phagocytosis of Sickle Erythrocytes: Immunologic and Oxidative Determinants of Hemolytic Anemia," *Blood* 64:733 (1984).

Some agents have been investigated that appear to interfere with adhesion. For example, Smith et al. describe the use of Fluosol DA, a perfluorodecalin-perfluorotripropylamine product, and its emulsifier, Pluronic F-68; they report that these agents abolished sickle cell adherence to endothelium in vitro. See C. M. Smith et al. "Pluronic F-68 Reduces the Endothelial Adherence and Improves the Rheology of Liganded Sickle Erythrocytes," *Blood* 69:1631 (1987). Unfortunately, Pluronic is a potent activator of complement even at low concentrations, and adverse pulmonary reactions have been observed in humans after the clinical administration of perfluorochemicals emulsified with Pluronic.

The chemotherapeutic agent hydroxyurea has had some success. However, it appears that hydroxyurea delays—but does not prevent—the onset of crises and that this drug is effective in only a subset of patients with sickle cell disease. See S. Charache et al. "Effect of Hydroxyurea on the Frequency of Painful Crisis in Sickle Cell Anemia," *New Eng. J. Med.* 332:1317 (1995) (hydroxyurea treated patients displayed a median time to first crisis of three months compared to one and one-half months in untreated controls).

Thus, no effective treatment for vaso-occlusive crisis has been described. Current therapy for crisis is supportive, including the use of supplemental oxygen, analgesics, and antibiotics (where infection is suspected). In addition, the diagnosis of vaso-occlusive crisis is usually made on clinical grounds; there are at present no laboratory tests diagnostic of crisis in patients with sickle cell disease. Clearly, there is a great need for new approaches to the diagnosis and treatment of vaso-occlusive crisis in sickle cell disease.

SUMMARY OF THE INVENTION

The present invention relates to methods for treating sickle cell disease, and in particular, detection and treatment of vaso-occlusive crisis in sickle cell disease. In accordance with the present invention, density centrifugation, lymphocyte/erythrocyte conjugate and mixing assays, and antibodies which bind CD2 and CD58 are selectively employed to detect and treat sickle cell crises.

With respect to detecting crises, the present invention contemplates measuring the incidence of preformed lymphocyte/erythrocyte conjugates in blood from patients with sickle cell disease. The present inventors have made the novel observation that patients with sickle cell disease display increased adhesion of sickle red blood cells to autologous lymphocytes. While the benefits of the present invention do not rely on an understanding of precise disease mechanisms, it is believed that sickle lymphocyte/erythrocyte conjugates could contribute to the pathophysiology of vaso-occlusive crisis directly, by serving to occlude the microvasculature, and/or indirectly, by releasing activation molecules (e.g., cytokines) that could stimulate cells in the microvasculature (e.g., endothelial cells, neutrophils, platelets, and monocytes) and promote vaso-occlusion.

In another embodiment, the present invention contemplates mixing autologous lymphocytes in vitro with sickle red blood cells and assessing the degree of lymphocyte/erythrocyte adhesion, as well as the ability of anti-CD2 and anti-CD58 antibodies to inhibit such adhesion.

With respect to treating, the present invention contemplates both prophylactic and acute treatment. While not limited by the nature of the mechanism by which a therapeutic effect is achieved, it is believed that the treatment method of the present invention is expected to have an inhibitory effect on sickle lymphocyte/erythrocyte adhesion and, consequently, on vaso-occlusive crisis—however, without the toxicity associated with other agents. In one embodiment, this in vivo method comprises administering a therapeutic preparation comprising antibodies reactive with CD2 and/or CD58 to a patient with sickle cell disease.

In one embodiment, the present invention contemplates a method of testing blood, comprising: a) providing blood from a patient with sickle cell disease; and b) examining said blood for preformed lymphocyte/erythrocyte conjugates. It is preferred that prior to said examining, said blood is subjected to density centrifugation under conditions such that a cell layer is generated comprising predominantly lymphocytes. Moreover, it is preferred that after said centrifugation and prior to said examining, at least a portion of said lymphocytes is removed from said layer, and placed on a microscope slide so that said examining is performed microscopically. In accordance with the present invention, the number of lymphocytes with at least one adherent erythrocyte are counted.(and expressed as the percent of lymphocytes with adherent red blood cells).

In another embodiment, the present invention contemplates a method of testing blood, comprising: a) providing erythrocytes from a patient with sickle cell disease; b) providing autologous lymphocytes from said patient with sickle cell disease; and c) mixing said autologous lymphocytes and said erythrocytes in vitro to create a cell suspension under conditions such that lymphocyte/erythrocyte conjugates can form. It is preferred, prior to said mixing, that either said lymphocytes are exposed in vitro to antibody (such as anti-CD2 antibody) or said erythrocytes are exposed in vitro to antibody (such as anti-CD58 antibody).

In the mixing assay, it is preferred that said autologous lymphocytes and said erythrocytes are mixed in cell culture media at the ratio where there are more erythrocytes than lymphocytes, and more preferrably where the concentration of erythrocytes is at least approximately ten-fold greater than the concentration of lymphocytes (including where the ratio is approximately 1 lymphocyte to 100 erythrocytes). Typical culture conditions are used for the mixing assay (e.g., incubation of said cell suspension between approximately 20° C. and approximately 40° C., and more preferrably approximately 37° C.) and a variety of incubation times is contemplated (e.g., between approximately one minute and twenty-four hours, but more typically between approximately thirty minutes and one hour). After said incubation, said cell suspension is examined for lymphocyte/erythrocyte conjugates. Typically, prior to said examining, at least a portion of said cell suspension is removed and placed on a microscope slide so that said examining is performed microscopically, and the number of lymphocytes with at least one adherent erythrocyte is counted (and expressed as the percent of lymphocytes with adherent red blood cells). A portion of said cell suspension may, alternatively, be examined by flow cytometry.

The present invention contemplates both ex vivo and in vivo treatments. One embodiment of the ex vivo method of the present invention comprises: i) withdrawing whole blood from the subject; ii) forming the blood into an extracorporeal stream; iii) flowing the stream through a treatment station; iv) adding inhibitory antibodies or antibody analogues (and/or physically removing preformed lymphocyte/erythrocyte conjugates); and v) returning the treated whole blood to the subject. One embodiment of the in vivo method of the present invention comprises administering inhibitory antibodies or antibody analogues to a patient with sickle cell disease in therapeutically effective amounts, such that the formation of autologous lymphocyte/erythrocyte conjugates is inhibited. The present invention also contemplates using inhibitory antibodies (such as CD2- and CD58-reactive antibodies or antibody analogues) in combination with other pharmaceuticals to treat sickle cell disease. In one embodiment, this in vivo method comprises administering a therapeutic preparation comprising antibodies (or antibody analogues) reactive with CD2 and/or CD58. It is not intended that the present invention be limited to complete inhibition; any inhibition of conjugate formation is deemed of benefit.

In one embodiment of the treatment method, the present invention contemplates a method of treating blood, comprising: a) providing blood from a patient with sickle cell disease; and b) removing, from said blood, preformed lymphocyte/erythrocyte conjugates. It is not intended that the present invention be limited by the method of removal. Physical removal may be achieved by filtration, sieving, or affinity interactions. Alternatively, removal may be achieved by leukapheresis using commercially available apheresis machines. It is not intended that the present invention be limited to complete removal; any reduction in preformed conjugates is deemed of benefit.

DESCRIPTION OF THE INVENTION

The present invention relates to methods for treating sickle cell disease, and in particular, for detection and treatment of vaso-occlusive crisis in sickle cell disease. The present inventors have made the novel observations that: 1) patients with sickle cell disease display increased red blood cell adhesion to autologous lymphocytes, and 2) this adhesion can be inhibited with specific antibodies. The description of the invention is divided into the following sections: A) Lymphocyte/Erythrocyte Adhesion; B) Sickle Cell Adhesion Assays; C) Inhibiting Lymphocyte/Erythrocyte Adhesion In Vitro with Antibodies; D) Prophylactic Treatment of Patients with Sickle Cell Disease; E) Ex Vivo Treatment of Vaso-occlusive Crisis; and F) In Vivo Treatment of Vaso-occlusive Crisis.

It is not intended that the present invention be limited by the underlying genetic basis for sickle cell disease. Indeed, there are sickle syndromes other than homozygous hemoglobin S disease that are associated with crisis (e.g., hemoglobin SC disease or hemoglobin S/beta-thalassemia) and that can be treated with success using the methods of the present invention.

A) Lymphocyte/Erythrocyte Adhesion

Researchers have made some progress in mapping out cellular and molecular interactions of human lymphocytes, including those that involve macromolecules which may act as chemical signals to coordinate lymphocyte actions and functions. The modern view of immunology has the T-cell as a key player in the body's specific defense mechanism. Two particular classes of T-cells, the helper T-cell ($T_H$) and the cytotoxic T-cell ($T_c$), play important roles in the both the humoral and the cell-mediated immune response.

Great attention has been focused on T cell surface receptors and their associated ligands. One such receptor/ligand pair is CD2 on T cells and lymphocyte function-associated antigen 3 (or "LFA-3" also known as CD58) on target or stimulator cells. See F. Sanchez-Madrid et al., "Three Distinct Antigens Associated with Human T-Lymphocyte-Mediated Cytolysis: LFA-1, LFA-2, and LFA-3," Proc. Nat. Acad. Sci. 79:7489 (1982). The physiological role of the CD2/CD58 interaction is thought to involve antigen-independent adhesion between T cells and potential target or stimulator cells. Resting human T cells do not bind autologous erythrocytes in normal individuals. It has been reported that normal T cells, upon activation, can bind autologous erythrocytes in vitro via an interaction between CD2, found on T cells, and LFA-3, found on red cells. See M. L. Plunkett et al., "Rosetting of Activated Human T-Lymphocytes with Autologous Erythrocytes. Definition of the Receptor and Ligand Molecules as CD2 and Lymphocyte Function-Associated Antigen 3 (LFA-3)," J. Exp. Med. 165:664 (1987).

Other membrane bound ligands have been reported on the cell surface of normal erythrocytes. For example, CD36, an adhesion molecule found on platelets, monocytes and some types of endothelial cells, has been reported on normal human erythrocytes. See M. R. van Schravendijk et al., "Normal Human Erythrocytes Express CD36, an Adhesion Molecule of Monocytes, Platelets, and Endothelial Cells," Blood 80:2105 (1992).

B) Sickle Cell Adhesion Assays

As noted previously, the present inventors have made the novel observation that patients with sickle cell disease display increased red blood cell adhesion to autologous lymphocytes. While the observation was made first by detection of preformed lymphocyte/erythrocyte conjugates in mononuclear cell fractions generated by density centrifugation of blood from patients with sickle cell disease, the findings have been confirmed and extended in in vitro mixing assays. Importantly, normal (unactivated) lymphocytes do not react with autologous red blood cells. Moreover, when the patients with sickle cell disease were separated into patients not in crisis, patients in acute crisis, and patients several days after the onset of crisis, it was found that patients in acute crisis have a significantly greater fraction of preformed conjugates (i.e., conjugates of autologous lymphocytes with adherent red cells) than both: i) patients not in crisis; and ii) patients several days after the onset of crisis. Because of the latter finding, the present invention contemplates the measurement of preformed conjugates as a means of detecting acute crisis as well as the onset of acute crisis. The present invention also contemplates measuring binding between sickle red blood cells and autologous lymphocytes in an in vitro mixing assay. Regardless of which of the two assays is used, the present invention contemplates, as diagnostic of acute crisis, an observation of approximately twenty (20) percent (%) of lymphocytes with adherent sickle red blood cells.

C) Inhibiting Lymphocyte/Erythrocyte Adhesion In Vitro with Antibodies

The present invention also contemplates the use of antibodies (whether monoclonal or polyclonal) which bind CD2 and CD58 in the above-described in vitro mixing assay. Specifically, the present invention contemplates the use of such antibodies to confirm specific lymphocyte/erythrocyte interaction by inhibiting adhesion. Inhibition of cell adhesion using these specific antibodies (and the lack of inhibition using other antibodies) indicates the presence of specific cell-cell adhesion.

D) Prophylactic Treatment of Patients with Sickle Cell Disease

The present invention contemplates the use of CD2- and CD58-reactive antibodies or antibody analogues (see below) to prevent sickle red blood cell adhesion to autologous lymphocytes in vivo. The present invention contemplates the use of anti-CD2 and anti-CD58 antibodies, whether together or separate, or in a therapeutic preparation with other compounds and agents. While the benefit conveyed by treatment according to the present invention is not dependent on the understanding of the mechanism(s) by which antibodies achieve a therapeutic result, it is believed that competitive binding of the exogenously supplied antibodies prevents adhesion of lymphocytes to erythrocytes in sickle cell disease patients, thereby directly or indirectly preventing vaso-occlusion by lymphocyte/erythrocyte adhesion conjugates.

The present invention also contemplates preventing sickle cell crisis by the use of immunosuppressive agents. While the benefit conveyed by immunosuppressive treatment according to the present invention is not dependent on the understanding of the mechanism(s) by which a therapeutic result is achieved, it is believed that exogenously supplied immunosuppressive agents cause T cells to remain unactivated so as to prevent adhesion of T cells to erythrocytes in sickle cell disease patients, thereby preventing vaso-occlusion by lymphocyte/erythrocyte adhesion conjugates.

The present invention is not limited by the particular immunosuppressive agent. In one embodiment, the immunosuppressive agent is Cyclosporin A (CsA) (commercially available from Sandoz Inc.) whose strong in vivo immunosuppressive effects were first discovered in trials using mice which led to successful clinical trials. CsA is now routinely used to suppress the immune response for procedures such as organ transplantation. One of the attractive properties of cyclosporin A is that, unlike other previous immunosuppressive drugs, it does not show a general inhibition of cell proliferation. Only lymphocytes are inhibited, and the drug is not cytotoxic to those lymphocytes.

A strongly hydrophobic undecapeptide, CsA suppresses both humoral and cell-mediated immunity. It is generally believed that CsA inhibits a relatively early step of lymphocyte proliferation, before the initiation of DNA synthesis, and does not inhibit the cytotoxicity or response of T or B cells which have been already primed by interleukin-2. The precise mode of action of CsA has not been fully elucidated as of present but it is agreed upon that: 1) CsA binds mainly to cyclophilin, an abundant cytoplasmic protein, in the cell; 2) CsA affects internal cell $Ca^{2+}$ sensitivity; and 3) a combination of these properties as well as other unknown steps may lead to reduced production of interleukins and other cytokines in the cell, which would lead to decreased lymphocyte activation and proliferation. (See *Cyclosporin, Mode of Action and Clinical Application*, Thomson: Kluwer Academic Publishers, 1989; *Cyclosporine, Biological Activity and Clinical Applications*, Kahan: Elsevier Biomedical Press, 1982; and *Cyclosporin A*, White: Grune & Stratton, 1984).

Phenotyping of the lymphocytes involved in lymphocyte/erythrocyte conjugates has been performed. The results are shown in the table below.

| | |
|---|---|
| CD2 | + |
| CD3 | + |
| CD4 | + |
| CD8 | − |
| CD19 (B-cell marker) | − |
| CD25 (IL-2 receptor) | + |
| CD36 (Thrombospondin receptor) | − |
| CD56 (NK Cell Marker) | − |
| CD71 (Transferrin Receptor) | + |
| VLA-4/α4β1 (FN receptor) | + |

The phenotyping results indicate that the lymphocyte involved in such conjugates is a helper T cell, and that the T cell may be in an activated state.

E) Ex Vivo Treatment of Vaso-occlusive Crisis

The present invention contemplates ex vivo treatment of blood from patients with sickle cell disease to treat and/or prevent vaso-occlusive crisis. In one embodiment, the method of the present invention involves the addition of anti-CD2 and/or anti-CD58 antibodies (whether monoclonal or polyclonal) or antibody analogues (see below) to a modular blood bag for subsequent mixing in solution with unfractionated blood (e.g., whole blood) or fractionated blood (e.g., packed red blood cells, etc.). Following treatment, the treated blood is placed in storage for later transfusion or prepared immediately for transfusion. In the preferred embodiment, the present invention contemplates the return of the blood to the same subject from whom it was withdrawn.

Furthermore, the present invention is not limited to a "batch" method. In one embodiment, the present invention contemplates a "continuous" ex vivo treatment method. In this embodiment, the present invention contemplates forming a stream of blood and the step of flowing the stream past a treatment station. Such continuous flow systems are known for externally treating human blood (i.e., for treatments other than those described herein). For example, U.S. Pat. No. 4,321,919 to R. L. Edelson, hereby incorporated by reference, describes methods and devices for externally treating human blood involving: i) withdrawing whole blood from the subject; ii) treating the withdrawn whole blood; and iii) returning the treated whole blood to the subject. The Edelson patent also describes creating an extracorporeal stream and flowing said stream through a treatment station.

In the method of the present invention, the treatment station functions to add inhibitory antibodies or antibody analogues (see below). Alternatively, the treatment station may function to physically remove existing lymphocyte/erythrocyte conjugates. Removal may be achieved by affinity interactions between the conjugates and suitable ligands, or by filtration based on the relatively large particle size of the conjugates as compared to unconjugated lymphocytes, red blood cells, and platelets.

In one embodiment, physical removal is accomplished by leukapheresis, i.e., the removal of the lymphocytes (including the lymphocytes with adherent red blood cells) from the blood product. Commercially available apheresis machines are contemplated for this purpose. Such machines can be wheeled to the bedside and involve connecting sterile tubing sets, also called pheresis sets, to the patient or donor. As the blood is pumped into the machine, an anticoagulant (e.g., acid citrate dextrose) is automatically added, and the blood enters the centrifugation chamber. In the chamber, centrifugation is used to separate components: the denser layers (red blood cells) are separated from the less dense layers (white blood cells, plasma), and the desired layers are siphoned into collection bags. Optical sensors detect plasma-cell interfaces to minimize contamination from other components.

Commercially available machines also perform intermittent centrifugation, centrifuge blood to separate the components, and then reinfuse the desired components through the same line (requiring one venipuncture). Units that perform continuous centrifugation continually withdraw and process small volumes of blood, requiring two venipunctures to perform uninterrupted removal and return of blood components.

F) In Vivo Treatment of Vaso-occlusive Crisis

While the present invention contemplates ex vivo treatment (see above), in vivo treatment is also contemplated. In one embodiment, anti-CD2 and/or CD58 antibodies (whether monoclonal or polyclonal) or antibody analogues (see below) are administered directly to a patient with sickle cell disease (e.g., intravenous administration).

The present invention is not limited to the administration of intact antibodies. Indeed, the present invention contemplates the use of antibody analogues. Antibody analogues are those compounds which act in an analogous manner to inhibit lymphocyte/erythrocyte adhesion (i.e., they are defined functionally and not limited structurally). They may include (but are not limited to) peptides, peptide-mimetics, and other small molecules.

The present invention is also not limited to a particular therapeutic preparation. The present invention contemplates using therapeutic compositions of CD2- and CD58-reactive antibodies (or antibody analogues) to delay, prevent and/or treat sickle cell crises. As noted above, the present invention also contemplates using antibodies in combination with other pharmaceuticals in a therapeutic preparation to treat sickle cell disease.

Where combinations are contemplated, it is not intended that the present invention be limited by the particular nature of the combination. The present invention contemplates combinations as simple mixtures as well as chemical hybrids. An example of the latter is where the antibody is covalently linked to a pharmaceutical. Covalent binding can be accomplished by any one of many commercially available crosslinking compounds.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to humans in a manner similar to other therapeutic agents. In general, the dosage required for therapeutic efficacy will vary according to the type of use and mode of administration, as well as the particularized requirements of individual patients.

Compositions are typically prepared as liquid solutions or suspensions. Formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared.

The antibodies of the present invention are often mixed with diluents or excipients which are physiological, tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); gm (grams); mg (milligrams); µg (micrograms); L (liters); ml (milliliters); µl (microliters); cm (centimeters); mm (millimeters); µm (micrometers); nm (nanometers); ° C. (degrees Centigrade).

In the Examples below, the testing of patient blood is described. Patients with confirmed sickle cell disease attending the Sickle Cell Disease Unit at Brigham and Women's Hospital for normal outpatient checks and patients admitted to the hospital in vaso-occlusive crisis were selected. Blood was obtained from patients and normal controls by venipuncture, using heparin as an anticoagulant. Blood was maintained at 21° C. and processed within one hour.

In some of the Examples below, purified lymphocytes are employed in mixing assays. To obtain purified lymphocytes, whole blood from sickle cell disease patients and normal controls was carefully layered in separate Accuspin System-Histopaque-1077 centrifuge tubes (Sigma, St. Louis, Mo.) and centrifuged at 2450 rpm (1000×g) for 10 minutes at 21° C. (per instructions of the manufacturer). Mononuclear cells formed a single band at the Histopaque-plasma interphase. In contrast, red blood cells and granulocytes passed through the filter barrier and formed a pellet at the bottom of the tube. Mononuclear cells and plasma were carefully aspirated with Pasteur pipets and collected separately. Mononuclear cells isolated by this method contained greater than 87% lymphocytes, as assessed by Wright's stain and differential counting. Mononuclear cells were suspended in medium consisting of RPMI 1640 supplemented with 10% autologous plasma, L-glutamine (2 mM) and penicillin-streptomycin solution (complete RPMI medium).

EXAMPLE 1

The present inventors have made the novel observation that patients with sickle cell disease display increased sickle red blood cell adhesion to autologous lymphocytes. The initial finding was made following density centrifugation of blood from sickle cell disease patients; the mononuclear cell band in Accuspin tubes (see above) from sickle blood was found to be red in color. In contrast, the mononuclear cell band from normal blood was milky white. To determine the cellular basis for this color change, 10 µl of mononuclear cells were placed on a slide without further treatment, gently covered with a coverslip and sealed on the slide using nail polish. Cells were observed using a Zeiss Axioskop microscope (Carl Zeiss, Inc., Thornwood, N.Y.) with differential interference contrast optics. Monocytes and platelet aggregates in the mononuclear preparation adhered spontaneously to the glass slide. In contrast, lymphocytes were non-adherent and free floating on the glass slide. Lymphocyte phenotype was confirmed by Wright's stain and differential counting. Sickle red blood cells were found to be adherent to free floating autologous lymphocytes. Adhesion was confirmed by subjecting the adherent cells to mild shear stress, obtained by gently focusing the oil immersion objective up and down against the glass cover slip. Adherent cells remained attached during this experimental maneuver, whereas non-adherent cells floated away from one another. Lymphocyte/erythrocyte adhesion was not observed in control mononuclear preparations.

The degree of lymphocyte/erythrocyte adhesion was assessed in vitro. Briefly, seven (7) patients with sickle cell disease were tested along with four (4) normal controls in the in vitro mixing assay of the present invention. Packed red blood cells were added at physiological ratios (100 RBCs:1 lymphocyte) to 500 µl of an autologous lymphocyte suspension in complete RPMI medium. The cell suspension was then incubated at 37° C. for 45 minutes with frequent mixing. After incubation, slides were prepared and observed using differential interference contrast microscopy. The percent of lymphocytes with at least one adherent red blood cell was scored microscopically. At least 200 cells were counted in each sickle mononuclear slide, and 1000 cells were counted in each control sample. Slides were counted on four separate occasions by two independent observers who were blinded to the test conditions.

Figure 1:
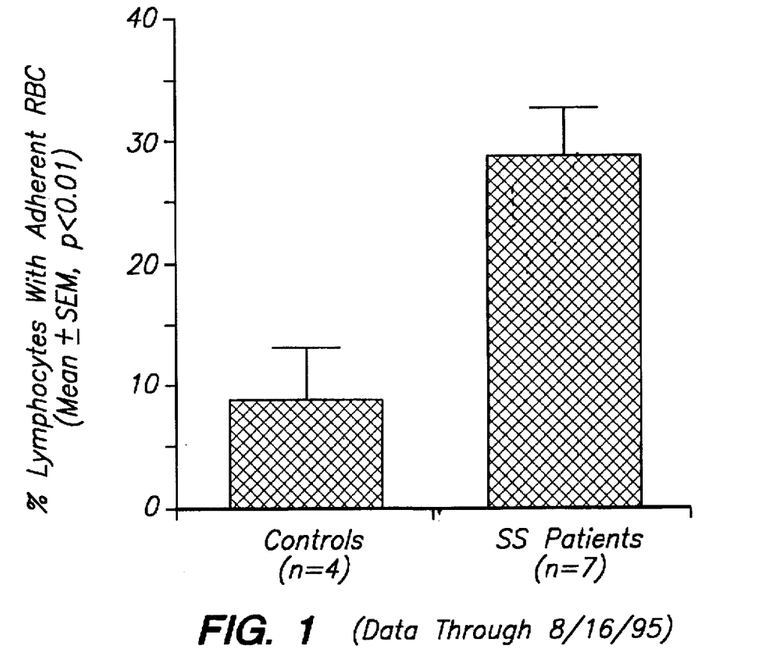
FIG. 1 is a bar graph showing the results of mixing autologous lymphocytes in vitro with red blood cells from seven (7) patients with sickle cell disease and four (4) control individuals.

FIG. 1 is a bar graph showing the results of the in vitro mixing assay; significantly more red blood cells adhere to autologous lymphocytes in the sickle cell disease group, relative to the control group. The average percent of lymphocytes with at least one adherent red blood cell in the sickle cell disease patient group is greater than approximately twenty (20) percent (%) and, more specifically is approximately twenty-five (25) percent (%).

Figure 2:
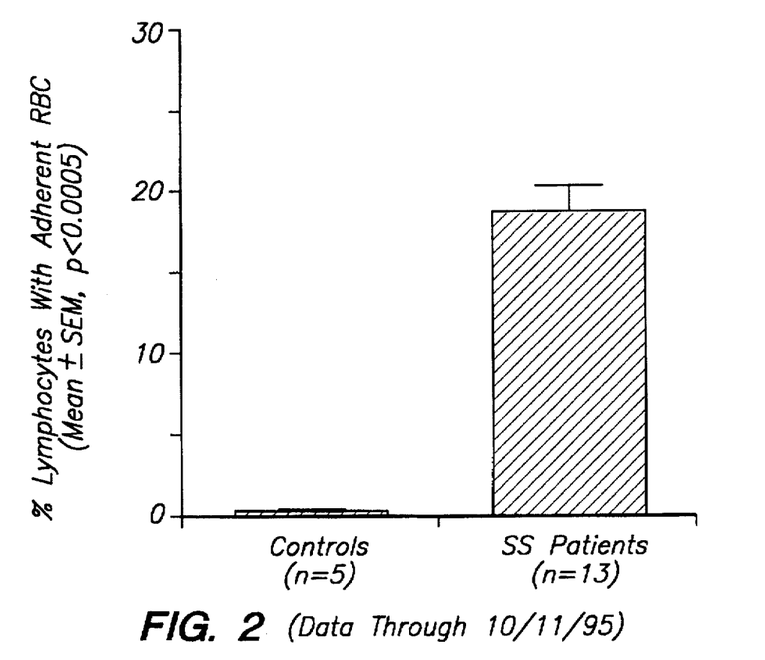
FIG. 2 is a bar graph showing the incidence of preformed lymphocyte/erythrocyte conjugates in mononuclear cell fractions isolated from the blood of thirteen (13) patients with sickle cell disease and five (5) controls.

FIG. 2 is a bar graph showing the incidence of preformed lymphocyte/erythrocyte conjugates in mononuclear cell fractions isolated from the blood of thirteen (13) patients with sickle cell disease and five (5) controls. The average percent of lymphocytes with at least one adherent red blood cell in the patient group is greater than approximately fifteen (15) percent (%). The control group shows virtually no preformed conjugates (i.e., conjugates of erythrocytes and autologous lymphocytes). Clearly, normal (unactivated) lymphocytes do not react with autologous normal red blood cells. Interestingly, preliminary experiments indicate that normal (non-sickle) red blood cells adhere to sickle lymphocytes (data not shown), suggesting that lymphocytes from patients with sickle cell disease may be in an activated state.

Figure 3:
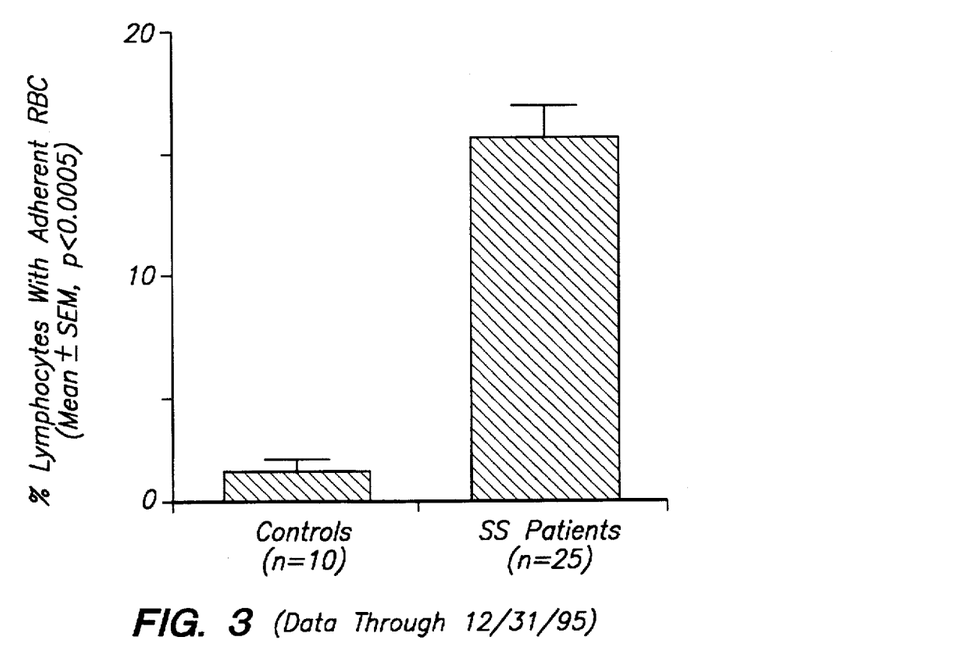
FIG. 3 is a bar graph showing the data measuring the incidence of preformed lymphocyte/erythrocyte conjugates from FIG. 2, together with data from an additional twelve (12) patients with sickle cell disease (for a total of twenty-five patients), and from an additional five (5) controls (for a total of ten controls).

The findings regarding preformed conjugates have been confirmed and extended. FIG. 3 is a bar graph showing the data measuring the incidence of preformed lymphocyte/erythrocyte conjugates from FIG. 2, together with data from an additional twelve (12) patients with sickle cell disease (for a total of twenty-five patients) and from an additional five (5) controls (for a total of ten controls). Again, the average percent of lymphocytes with at least one adherent red blood cell in the patient group is greater than approximately fifteen (15) percent (%). Again, the control group shows virtually no preformed conjugates (i.e., conjugates of erythrocytes and autologous lymphocytes).

Figure 4:
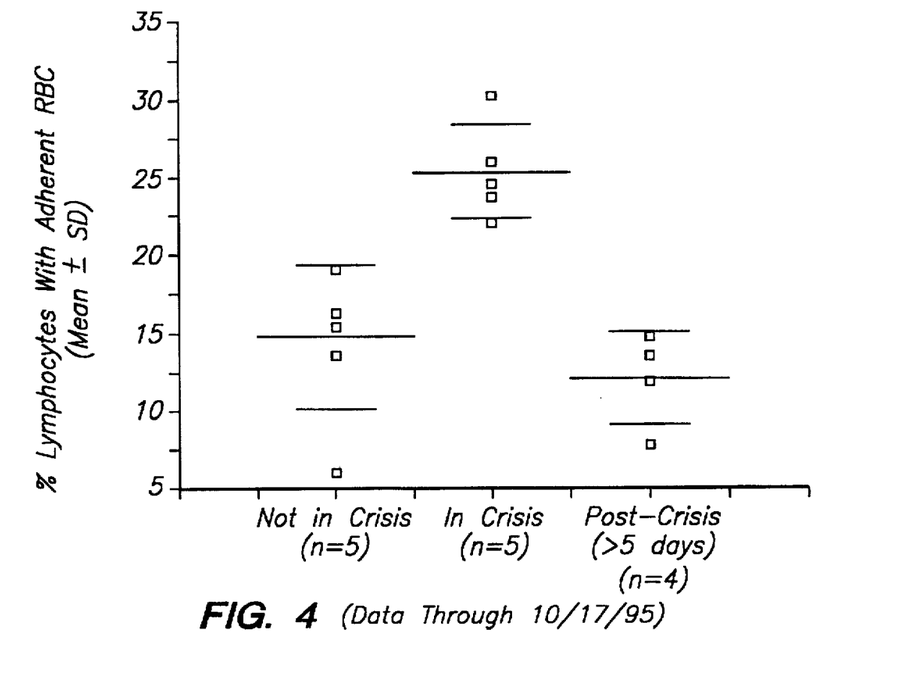
FIG. 4 is a plot comparing the incidence of preformed lymphocyte/erythrocyte conjugates from five (5) sickle cell disease patients in crisis, from five (5) patients not in crisis, and from four (4) patients post-crisis.
Figure 5:
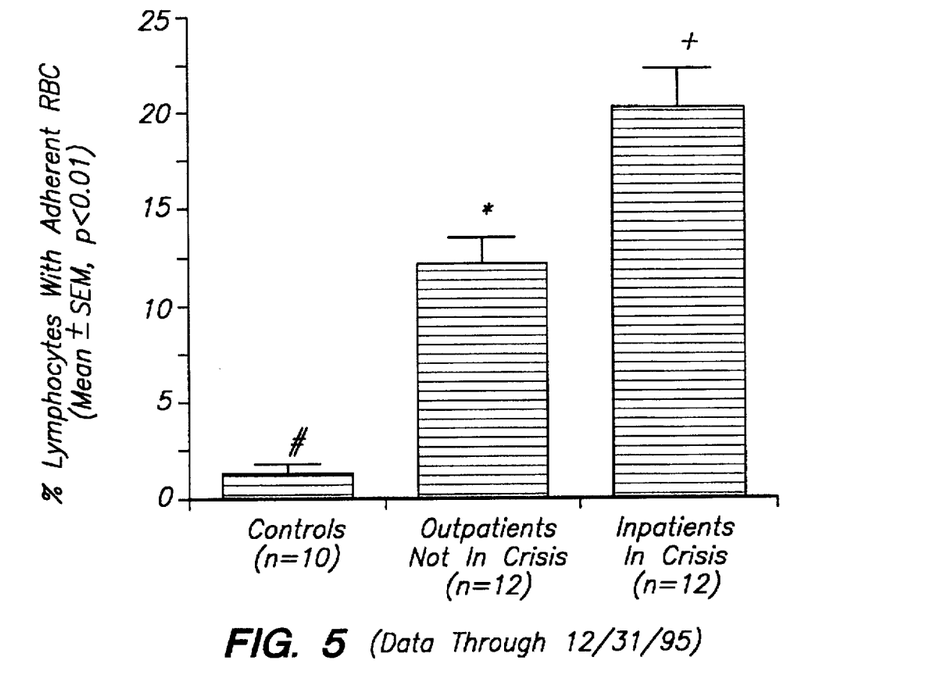
FIG. 5 is a graph comparing the incidence of preformed lymphocyte/erythrocyte conjugates using the data of FIG. 4 together with data from an additional seven (7) patients in crisis (for a total of twelve), from an additional seven (7) patients not in crisis (for a total of twelve), and from ten (10) controls.

In a further experiment, samples from patients with sickle cell disease were separated into samples from patients not in crisis, patients in acute crisis, and patients several days after the onset of crisis. FIG. 4 is a plot comparing the incidence of preformed lymphocyte/erythrocyte conjugates from five (5) sickle cell disease patients in crisis, from five (5) patients not in crisis, and from four (4) patients post-crisis. It is clear that patients in acute crisis have a significantly greater fraction of autologous lymphocytes with adherent red blood cells than both: i) patients not in crisis; and ii) patients several days after the onset of crisis. This result has been confirmed with additional patients and experiments. FIG. 5 is a graph comparing the incidence of preformed lymphocyte/erythrocyte conjugates using the data of FIG. 4 together with data from an additional seven (7) patients in crisis (for a total of twelve), from an additional seven (7) patients not in crisis (for a total of twelve), and from ten (10) controls.

The present invention contemplates the measurement of preformed conjugates (i.e., conjugates of sickle red blood cells and autologous lymphocytes) as a means of detecting the onset of acute crisis. As the cumulative data of these experiments show, an observation of approximately twenty (20) percent (%) of lymphocytes with adherent sickle red blood cells is diagnostic of acute crisis.

EXAMPLE 2

Figure 6:
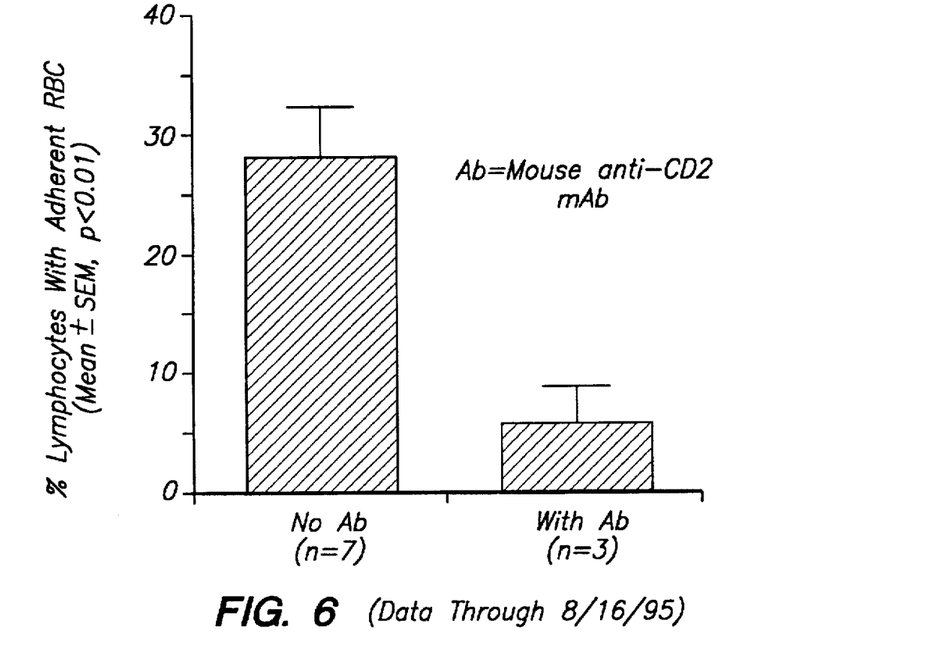
FIG. 6 is a bar graph showing that anti-CD2 antibodies prevent the adhesion of sickle erythrocytes to autologous lymphocytes in in vitro mixing assays.

In this example, the use of monoclonal anti-CD2 and anti-CD58 antibodies in in vitro mixing assays is described. In a first experiment, anti-CD2 antibody [commercially available from Endogen, Inc., Cambridge, Mass. as a mouse monoclonal anti-human CD2 purified antibody (IgG1, TS2-18 clone)] was used to reduce and/or completely inhibit the in vitro binding of lymphocytes to sickle red blood cells from three patients. In this experiment, lymphocytes were incubated with anti-CD2 antibody in complete RPMI medium at 21° C. for 30 minutes with mixing and the lymphocyte/erythrocyte mixing assay was then performed. FIG. 6 is a bar graph showing that anti-CD2 antibodies prevent the adhesion of sickle erythrocytes to purified autologous lymphocytes. Using the inhibiting antibody, the observed average percent of lymphocytes with adherent red blood cells was less than approximately five (5) percent (%).

Further experiments were performed using anti-CD2 and anti-CD58 antibodies, along with various other antibodies, including: 1) Mouse monoclonal anti-human CD58 (LFA-3) purified antibody (an IgG2a BRIC5 clone commercially available from Southern Biotechnology Associates, Inc., Birmingham, Ala.); 2) Mouse monoclonal anti-human VLA-4 (α4β1) purified antibody (an IgG1 antibody commercially available from Upstate Biotechnology, Inc., Lake Placid, N.Y.); 3) Mouse monoclonal anti-human Glycophorin A purified antibody (an IgG1 antibody commercially available from Immunotech, Inc., Westbrook, Me.); 4) Mouse monoclonal anti-human CD36 purified antibody (an IgG1 antibody also commercially available from Immunotech); 5) Mouse monoclonal anti-human CD58 purified antibody (an IgG2a L306.4 clone commercially available from Becton Dickinson Immunocytometry Systems, San Jose, Calif.); 6) Mouse monoclonal anti-human CD2 purified antibody (an IgG1 Leu-5b clone also commercially available from Becton Dickinson). In these experiments, lymphocytes were incubated with anti-CD2 antibody, and red blood cells were incubated with anti-CD58, anti-CD36, anti-VLA4, or anti-glycophorin A antibody, in complete RPMI medium at 21° C. for 30 minutes with mixing and the lymphocyte/erythrocyte mixing assay was then performed.

Figure 7:
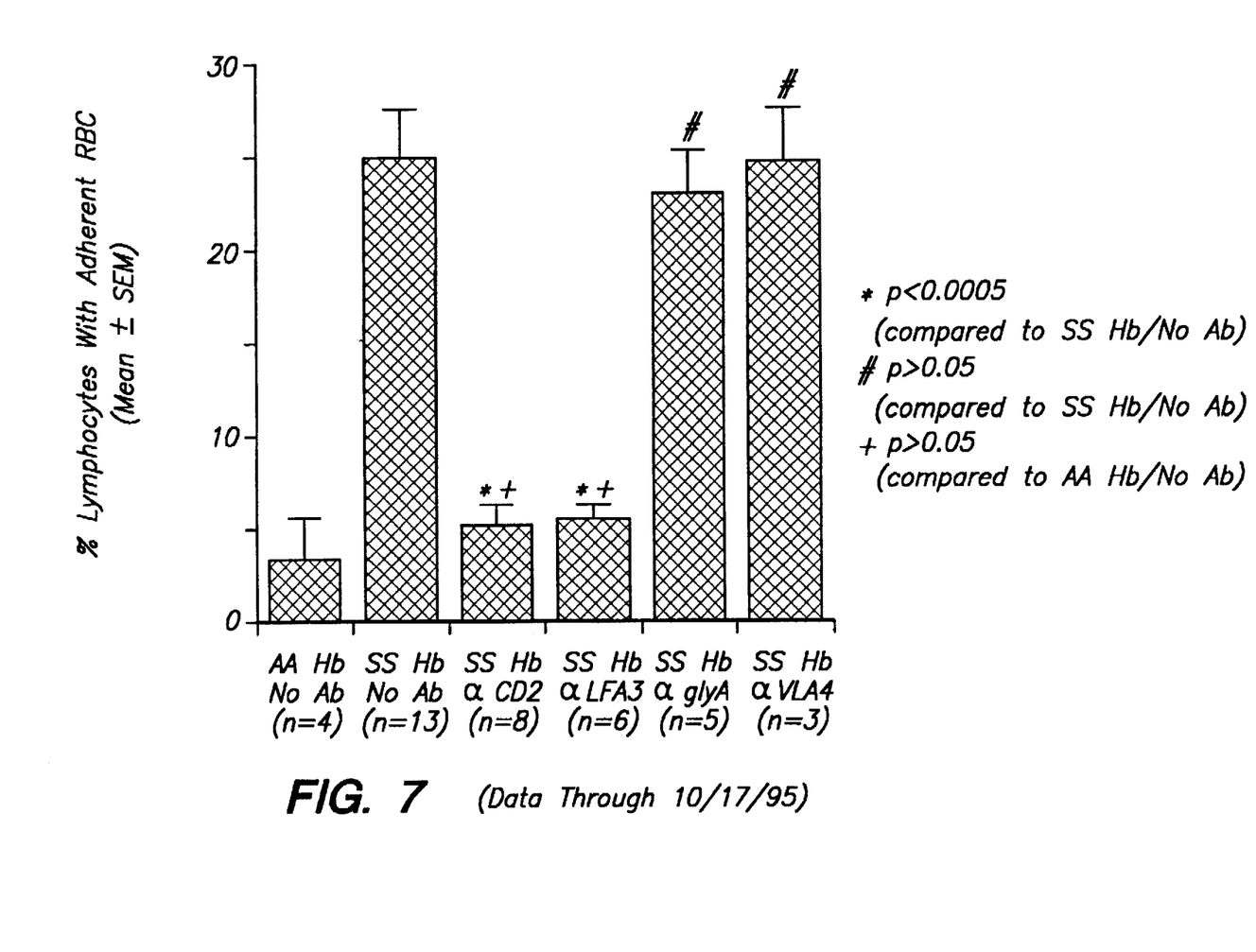
FIG. 7 is a bar graph showing the data from FIG. 6 for anti-CD2 antibody inhibition together with five (5) additional tests (for a total of eight mixing experiments with anti-CD2 antibody), along with data showing that anti-CD58 (LFA3) antibody specifically and competitively inhibits the adhesion of sickle erythrocytes to autologous lymphocytes.
Figure 8:
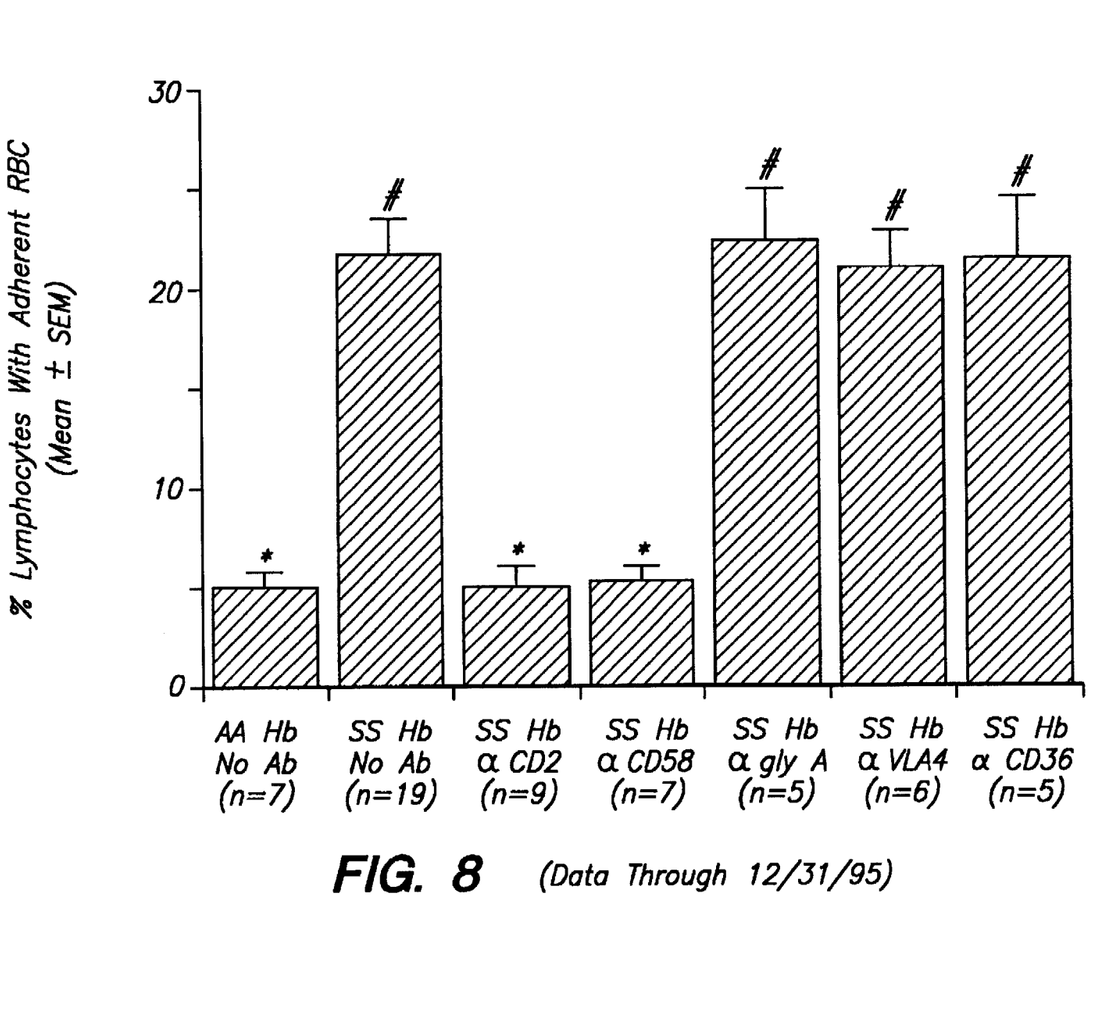
FIG. 8 is a bar graph showing the cumulative data from FIGS. 6 and 7 together with additional mixing experiments.

FIGS. 7 and 8 are bar graphs showing that anti-CD2 and anti-CD58 (LFA3) antibodies specifically and competitively inhibit the adhesion of sickle erythrocytes to autologous lymphocytes. Antibodies to other reported erythrocyte cell surface adhesion molecules, including glycophorin A, CD36 (see above) and VLA-4 (the fibronectin receptor), do not so inhibit the adhesion of sickle erythrocytes to autologous lymphocytes. The results of this example, while specific for CD2- and CD58-reactive antibodies, nonetheless show the general applicability of using such antibodies in conjunction with lymphocyte/erythrocyte mixing assays to screen for sickle cell crises.

EXAMPLE 3

The present invention contemplates ex vivo treatment of blood from patients with sickle cell disease to treat and/or avoid vaso-occlusive crisis. This example describes one embodiment, wherein the method involves the addition of anti-CD2 and/or CD58 antibodies (whether monoclonal or polyclonal) to a modular blood bag for subsequent mixing in solution with fractionated blood (i.e., packed red blood cells, etc.).

The present invention contemplates that the method is compatible with the standard blood product separation approach used presently in blood banks. In one embodiment, three bags are integrated by flexible tubing to create a blood transfer set (e.g., commercially available from Baxter, Deerfield, Ill.). After blood is drawn into the first bag, the entire set is processed by centrifugation (e.g., Sorvall™ swinging bucket centrifuge, Dupont), resulting in packed red blood cells and platelet rich plasma in the first bag. The plasma is expressed off of the first bag (e.g., using a Fenwall™ device for plasma expression), through the tubing and into the second bag.

The first bag can then be detached. In one embodiment, the third bag contains inhibiting antibody (e.g., anti-LFA3 antibody) diluted in media. Alternatively, a bag containing inhibiting antibody is sterile docked with the red blood cell bag. Sterile docking is well-known to the art. See e.g., U.S. Pat. No. 4,412,835 to D. W. C. Spencer, hereby incorporated by reference. See also U.S. Pat. Nos. 4,157,723 and 4,265,280, hereby incorporated by reference. Sterile docking devices are commercially available (e.g., Terumo, Japan).

It is not intended that the present invention be limited by the nature of the media used in connection with the inhibiting antibody. In one embodiment, commercially available synthetic media, plasmalyte-A (Baxter, Ill.), is used. Other commercially available media used routinely with red blood cells (and red blood cell storage) are also contemplated. Following treatment, the treated blood is placed in storage for later transfusion or prepared immediately for transfusion.

EXAMPLE 4

The present invention contemplates detection of preformed lymphocyte/erythrocyte conjugates and of lymphocyte/erythrocyte conjugates generated in mixing assays by flow cytometry. In flow cytometry, the increased size of the conjugates can be detected. Alternatively, antibodies bound to the conjugates are detected by the addition of fluorescently labeled secondary antibodies. The instrumentation measures the fluorescence intensity of each conjugate as it passes through a small orifice, and quantifies the fraction of fluorescently labeled lymphocytes that are present as conjugates with fluorescently labeled red blood cells.

To measure the conjugates using antibodies by flow cytometry, a small aliquot of a patient's blood is placed in buffer containing a binding antibody(ies) or control antibody. After incubation, secondary reagent(s) (e.g., anti-antibody(ies) conjugated to fluorophore(s) such as fluorescein and rhodamine) is then added to the tube in saturating mounts. Finally, the cells are diluted in isotonic saline, fixed with paraformaldehyde and analyzed using a FACSCAN (Becton Dickinson, Mountian View, Calif.).

From the above, it should be evident that the present invention provides a new approach to the diagnosis and treatment of vaso-occlusive crisis in sickle cell disease. Testing for preformed conjugates (or generating conjugates in mixing assays) allows for a convenient and simple laboratory test that is diagnostic of crisis in patients with sickle cell disease. Administration of conjugate-inhibiting antibody or antibody analogues (whether ex vivo or in vivo) allows for delay, prevention and/or treatment of crisis.

We claim:

1. A method of testing blood, comprising:
   a) providing blood from a patient with sickle cell disease; and
   b) examining said blood to determined the incidence of preformed lymphocyte/erythrocyte conjugates as a test for sickle cell crisis.

2. The method of claim 1, wherein prior to said examining, said blood is subjected to density centrifugation under conditions such that a cell layer is generated comprising lymphocytes.

3. The method of claim 2, wherein after said centrifugation and prior to said examining, at least a portion of said lymphocytes is removed from said cell layer.

4. The method of claim 3, wherein said portion is placed on a microscope slide so that said examining is performed microscopically.

5. The method of claim 4, wherein the number of lymphocytes with at least one adherent erythrocyte are counted.

6. A method of testing blood, comprising:
   a) providing i) erythrocytes from a patient with sickle cell disease; and ii) autologous lymphocytes from said patient with sickle cell disease;
   b) mixing said autologous lymphocytes and said erythrocytes in vitro to create a cell suspension under conditions such that lymphocyte/erythrocyte conjugates can form; and
   c) determining the incidence of lymphocyte/erythrocyte conjugates as a test for sickle cell crisis.

7. The method of claim 6, wherein, prior to said mixing, said lymphocytes are exposed in vitro to antibody.

8. The method of claim 7, wherein said antibody comprises anti-CD2 antibody.

9. The method of claim 6, wherein, prior to said mixing, said erythrocytes are exposed in vitro to antibody.

10. The method of claim 9, wherein said antibody comprises anti-CD58 antibody.

11. The method of claim 6, wherein said autologous lymphocytes and said erythrocytes are mixed in cell culture media at the ratio of approximately 1 lymphocyte to 100 erythrocytes.

12. The method of claim 11, wherein said conditions comprise incubation of said cell suspension at approximately 37° C.

13. The method of claim 12, wherein said incubation is carried out for between approximately one minute and twenty-four hours.

14. The method of claim 13, wherein said incubation is carried out for approximately one hour.

15. The method of claim 12, wherein after said incubation, said cell suspension is examined for lymphocyte/erythrocyte conjugates.

16. The method of claim 15, wherein, prior to said examining, at least a portion of said cell suspension is removed and placed on a microscope slide.

17. The method of claim 16, wherein said examining is performed microscopically and the number of lymphocytes with at least one adherent erythrocyte are counted.

* * * * *

UNITED STATES PATENT AND TRADEMARK OFFICE
CERTIFICATE OF CORRECTION

PATENT NO. : 5,669,396
DATED : 09/23/97
INVENTOR(S) : David Eric Golan et al.

It is certified that error appears in the above-indentified patent and that said Letters Patent is hereby corrected as shown below:

Col. 1, Line 4: Please insert --This invention was made with Government support under grant numbers HL 15157 and HL 32854 awarded by the National Institute of Health. The United States Government may have certain rights in this invention.--

Signed and Sealed this

Twenty-fifth Day of August, 1998

Attest:

BRUCE LEHMAN

*Attesting Officer*  *Commissioner of Patents and Trademarks*